US009226403B2

(12) United States Patent
Yi et al.

(10) Patent No.: US 9,226,403 B2
(45) Date of Patent: Dec. 29, 2015

(54) HYBRID ELECTRONIC SHEETS

(71) Applicant: KOREA INSTITUTE OF SCIENCE AND TECHNOLOGY, Seoul (KR)

(72) Inventors: Hyunjung Yi, Seoul (KR); Ki Young Lee, Seoul (KR); Chaun Jang, Busan (KR); Joonyeon Chang, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 0 days.

(21) Appl. No.: 14/325,928

(22) Filed: Jul. 8, 2014

(65) Prior Publication Data
US 2015/0305163 A1  Oct. 22, 2015

(30) Foreign Application Priority Data

Apr. 22, 2014 (KR) .................. 10-2014-0048348

(51) Int. Cl.
*C08L 5/08* (2006.01)
*C12N 11/14* (2006.01)
(Continued)

(52) U.S. Cl.
CPC . *H05K 3/007* (2013.01); *C08L 5/08* (2013.01); *C12N 11/14* (2013.01); *H05K 3/10* (2013.01); *H05K 2203/0786* (2013.01); *H05K 2203/12* (2013.01); *H05K 2203/122* (2013.01);
(Continued)

(58) Field of Classification Search
CPC .......... B82Y 5/00; B82Y 10/00; B82Y 15/00; B82Y 30/00; B82Y 40/00; H01L 51/0049; H01L 51/0093; H01L 51/426; H01L 51/444; Y02E 10/549; Y02E 10/542; H01G 9/2059; C01B 31/0273; C12N 2795/14131; C12N 11/14; H05K 3/007; H05K 3/10; H05K 2203/1305; H05K 2203/122; H05K 2203/0786; H05K 2203/12; H05K 2203/1333
See application file for complete search history.

(56) References Cited

U.S. PATENT DOCUMENTS 7,473,411 B2 * 1/2009 Ajayan et al. .............. 423/447.1
8,470,611 B2   6/2013 Dang et al.
(Continued)

FOREIGN PATENT DOCUMENTS

KR   101188172 B1   9/2012
KR   101325282 B1   10/2013

OTHER PUBLICATIONS

Xiangnan Dang, et al; "Virus-templated self-assembled single-walled carbon nanotubes for highly efficient electron collection in photovoltaic devices", Nature Nanotechnology, vol. 6, pp. 377-384; Published online: Apr. 24, 2011.
(Continued)

*Primary Examiner* — Nikolay Yushin
(74) *Attorney, Agent, or Firm* — Ladas & Parry LLP

(57) ABSTRACT

In accordance with the present disclosure, a hybrid electronic sheet which exhibits superior electrical property and allows biomaterial functionalization and flexible device patterning may be provided by binding a graphitic material in colloidal state to a biomaterial capable of binding thereto specifically and nondestructively. Since the electronic sheet is an electronic sheet wherein a biomaterial and an electrical material (graphitic material) are hybridized, it exhibits good compatibility with biomaterials and can be further functionalized with, for example, an enzyme that selectively reacts with a biochemical substance. Accordingly, an electrical material and a chemical or biological material may be effectively nanostructurized and it can be realized as a multi-functional, high-performance electronic sheet.

8 Claims, 14 Drawing Sheets

(51) Int. Cl.
*H05K 3/00* (2006.01)
*H05K 3/10* (2006.01)

(52) U.S. Cl.
CPC *H05K2203/1305* (2013.01); *H05K 2203/1333* (2013.01)

(56) References Cited

U.S. PATENT DOCUMENTS

| | | | |
|---|---|---|---|
| 2005/0147964 A1* | 7/2005 | Yamakawa et al. | 435/5 |
| 2005/0277160 A1 | 12/2005 | Shiba et al. | |
| 2006/0073089 A1* | 4/2006 | Ajayan et al. | 423/447.2 |
| 2007/0117147 A1* | 5/2007 | Jagota et al. | 435/7.1 |
| 2010/0069606 A1* | 3/2010 | Bangera et al. | 530/317 |
| 2012/0156688 A1* | 6/2012 | McAlpine et al. | 435/7.1 |
| 2012/0178640 A1* | 7/2012 | Strano et al. | 506/9 |
| 2013/0209807 A1 | 8/2013 | Chatterjee | |
| 2013/0230464 A1 | 9/2013 | Yi et al. | |
| 2014/0150855 A1* | 6/2014 | Inoue et al. | 136/254 |
| 2014/0197042 A1* | 7/2014 | Zhang et al. | 205/777.5 |
| 2014/0249052 A1* | 9/2014 | Mehmet et al. | 506/9 |
| 2014/0309126 A1* | 10/2014 | Yi et al. | 506/9 |
| 2015/0023858 A1* | 1/2015 | Tour et al. | 423/276 |

OTHER PUBLICATIONS

Sachedev S. Sidhu, et al; "High Copy Display of Large Proteins on Phage for Functional Selections", Journal Mol. Biol. vol. 296, pp. 487-495; Feb. 19, 2000; Mar. 14, 2012.

Hyunjung Yi, et al; "M13 Phage-Functionalized Single-Walled Carbon Nanotubes as Nanoprobes for Second Near-Infrared Window Flourescence Imaging of Targeted Tumors", Nano Letters, vol. 12, pp. 1176-1183.

Yun Jung Lee, et al; "Fabricating Genetically Engineered High-Power Lithium-Ion Batteries Using Multiple Virus Genes", Science, vol. 324, May 22, 2009, pp. 1051-1055.

Michael B. Zwick, et al; "The Maltose-Binding Protein as a Scaffold for Monovalent Display of Peptides Derived from Phage Libraries", Analytical Biochemistry, vol. 264, pp. 87-97, Article No. AB982793, Nov. 1, 1998.

Karen A. Noren, et al; "Construction of High-Complexity Combinatorial Phage Display Peptide Libraries", Methods, vol. 23, pp. 169-178, Feb. 2001.

Cheol-Hwan Park, et al; "Anisotroic behaviours of massless Dirac fermions in graphene under periodic potentials", Nature physics, vol. 4, pp. 213-217; Published online Feb. 24, 2008.

Seung-Wuk Lee, et al; "Chiral Smetic C Structures of Virus-Based Films", Langmuir, vol. 19, pp. 1592-1598, Published on Web Dec. 24, 2002.

Bong Gill Choi et al., "Solution Chemistry of Self-Assembled Graphene Nanohybrids for High-Performance Flexible Biosensors", ACS Nano vol. 4 No. 5, Apr. 8, 2010, pp. 2910-2918.

Wenzhao Jia et al., "Electrochemical Tattoo Biosensors for Real-Time Noninvasive Lactate Monitoring in Human Perspiration", Anal. Chem. vol. 85., Jul. 1, 2013, pp. 6553-6560.

Zhuangchun Wu et al., "Transparent, Conductive Carbon Nanotube Films", Science vol. 305, Aug. 27, 2004, pp. 1273-1276.

Huanfen Yao et al., "A contact lens with embedded sensor for monitoring tear glucose level", Biosensors and Bioelectronics, Dec. 31, 2010, vol. 26, pp. 3290-3296.

B.M. Paschal; "Direct Submission", Submitted Oct. 19, 2007 Research Department, New England Biolabs, 240 County Road, Ipswich, MA 10938, USA, 5 pages.

\* cited by examiner

SWNT-M13 phage          SWNT-only

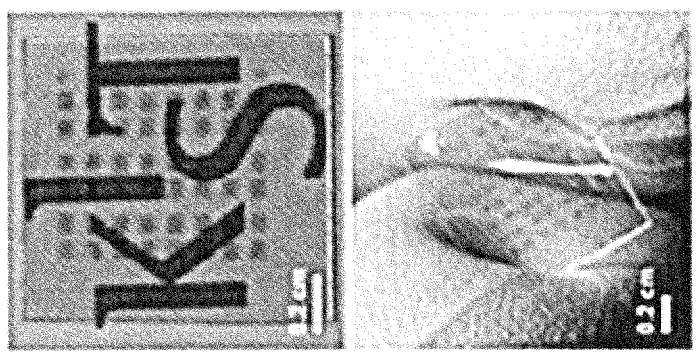
Fig. 6
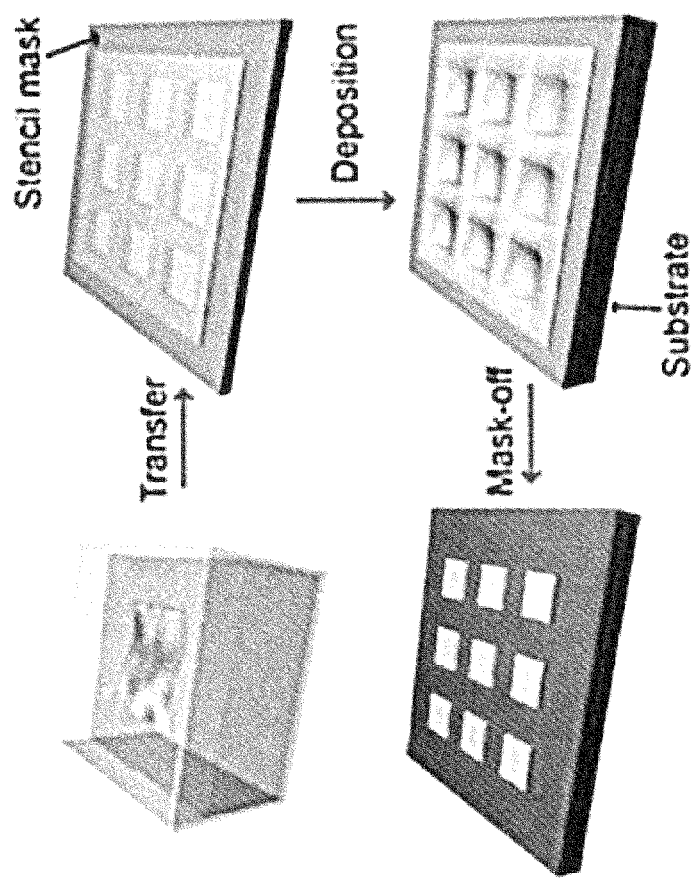

HYBRID ELECTRONIC SHEETS

CROSS-REFERENCE TO RELATED APPLICATION

This application claims priority to Korean Patent Application No. 10-2014-0048348, filed on Apr. 22, 2014, and all the benefits accruing therefrom under 35 U.S.C. §119, the contents of which in its entirety are herein incorporated by reference.

BACKGROUND

1. Field

The present disclosure relates to a hybrid electronic sheet and a method for preparing the same.

2. Description of the Related Art

Researches on flexible high-performance materials and devices such as wearable computers, bendable displays, wearable biomedical electrodes and biosensors for health monitoring, human-robot interfaces, etc. are rapidly increasing nowadays. For such applications, development of a material which has excellent electrical property as well as superior mechanical property and to which biochemical or biological property can be further provided in addition to the electrical property, e.g., as in wearable biosensors, is of great importance. In addition, for realization of a high-performance device composed of various constituents on a flexible substrate, low contact resistance is required between the constituents and superior contact property with the flexible substrate is necessary.

Since carbon nanomaterials such as carbon nanotube, graphene, etc. have excellent electrical, mechanical and chemical properties, use of the materials as an electrode of flexible electronic devices, flexible bioelectrodes, sensors, flexible energy devices, etc. is actively studied recently.

For application of graphene or carbon nanotube to flexible devices, a process of transferring the graphene or carbon nanotube synthesized at high temperature without decrease in electrical property is essential. In addition, for effective operation of a high-performance device, effective electrical contact property between the carbon nanomaterial and other constituents of the device and resistance property on the flexible substrate are very important. Carbon nanotube is commonly used by depositing a film on a substrate, for example, by spin coating the carbon nanotube dispersed in an organic solvent or by forming a film through vacuum filtration and dissolving out the filter membrane chemically to obtain a carbon nanotube film. However, these methods are problematic in that the performance of the device is decreased or contact property with a flexible substrate is unsatisfactory due to an organic solvent or a dispersant remaining after chemical etching. Also, transfer onto a substrate with a complex shape is impossible because of large film thickness and patterning which is essential for realization of the device is difficult.

Graphene is used by growing the graphene on the surface of a metal such as copper by chemical vapor deposition (CVD) and transferring onto a desired substrate using an etching solution or by reducing chemically prepared graphene oxide through spin coating to obtain a reduced graphene oxide film. However, the CVD-grown graphene is disadvantageous in that use of an environmentally very harmful etching solution is necessary and effective surface area per unit area is very small because the graphene consists of a single or only a few layer(s). Further, because graphene is chemically stable, it is not easy to confer additional properties to the graphene. The reduced graphene oxide is disadvantageous in that electrical property is not excellent because a process of chemically reducing the graphene oxide which has been chemically oxidized is required.

When preparing a flexible electrode including a biomaterial such as a biosensor electrode, it is important to realize a high-performance flexible device without chemical etching. However, with the existing methods, it is difficult to realize a flexible device having superior electrical property wherein a biomaterial is nanohybridized.

SUMMARY

The present disclosure is directed to providing a hybrid electronic sheet which has superior and tunable electrical property, can be functionalized with a biomaterial and allows flexible device patterning. The present disclosure is also directed to providing a method for preparing the electronic sheet whereby a carbon nanomaterial having a graphitic surface is prepared into a thin hybrid electronic sheet with a large area in an aqueous solution without chemical etching.

In an aspect, the present disclosure provides a hybrid electronic sheet including a graphitic material and a biomaterial capable of binding to the graphitic material and an electronic device including the same.

In another aspect, the present disclosure provides a method for preparing a hybrid electronic sheet including a graphitic material and a biomaterial capable of binding to the graphitic material, including: preparing a mixture by mixing a colloid material including a graphitic material with a biomaterial capable of binding to the graphitic material; and forming an electronic sheet in an aqueous solution by dialyzing the mixture using a membrane.

In accordance with the present disclosure, a hybrid electronic sheet which exhibits superior, tunable electrical property and allows biomaterial functionalization and flexible device patterning may be provided by binding a graphitic material in colloidal state to a biomaterial capable of binding thereto specifically and nondestructively. Since the electronic sheet has a nondestructively controllable nanostructure, an electronic sheet having semiconductor property can be obtained from an electrically non-separated, hybrid single-walled carbon nanotube. Further, since the electronic sheet is an electronic sheet wherein a biomaterial and an electrical material (graphitic material) are hybridized, it exhibits good compatibility with biomaterials and can be further functionalized with, for example, an enzyme that selectively reacts with a biochemical substance. Accordingly, an electrical material and a chemical or biological material may be effectively nanostructurized. In addition, the electronic sheet is structurally stable and exhibits superior flexibility owing to good contact property after transfer onto a flexible substrate. Accordingly, it can be realized as a multi-functional, high-performance electronic sheet.

Furthermore, since the electronic sheet according to the present disclosure is prepared in an aqueous solution by dialyzing a mixture of the graphitic material and the biomaterial using a membrane, no chemical etching or additional carrier material layer is necessary for transference. Accordingly, it can be transferred even onto a polymer material with a complex shape (see FIG. 5b). In accordance with the present disclosure, a high-performance electronic sheet can be transferred onto various substrates. For example, a flexible electronic sheet exhibiting excellent electrochemical property, with 4 times or higher charging current even on a polymer substrate with a metal electrode layer than on Au, may be provided (see FIG. 7). Also, since patterning can be conducted easily using a substrate or a mask, a device can be prepared conveniently on a flexible substrate (see FIG. 9).

Accordingly, the hybrid electronic sheet can be usefully used in a flexible electronic device, an information processing or storage device or as a brain surface electrode, a flexible biosensor electrode an electrode for a flexible battery, etc.

BRIEF DESCRIPTION OF THE DRAWINGS

FIG. 6 schematically describes a method of forming a pattern of an electronic sheet using a stencil mask according to an exemplary embodiment of the present disclosure as well as images of the formed pattern.

DETAILED DESCRIPTION

In the present disclosure, a "graphitic material" refers to a material which has a surface wherein carbon atoms are arranged in a hexagonal shape, i.e. a graphitic surface. It is used in the broadest concept including any material having a graphitic surface, regardless of physical, chemical or structural properties.

In the present disclosure, a "biomaterial" refers to a material derived from a biological source which is capable of binding to the graphitic material. It is used in the broadest concept including any biomaterial, e.g. nucleic acid, peptide or protein, which binds selectively and specifically to the graphitic material, regardless of the mode of binding and biological or structural properties.

Hereinafter, the present disclosure is described in more detail.

The present disclosure provides a hybrid electronic sheet including a graphitic material and a biomaterial capable of binding to the graphitic material.

Figure 1A:
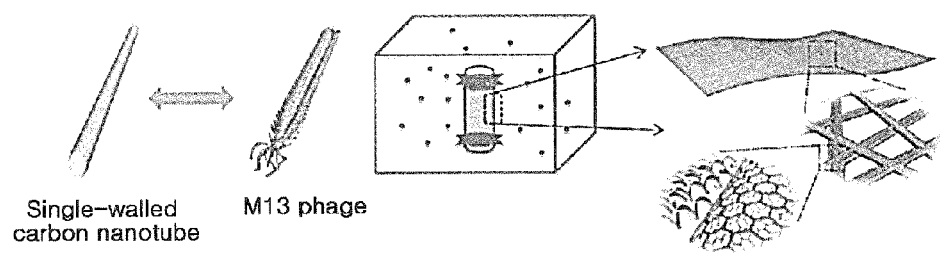
FIG. 1a schematically describes a process of preparing a hybrid electronic sheet according to an exemplary embodiment of the present disclosure.
Figure 1B:
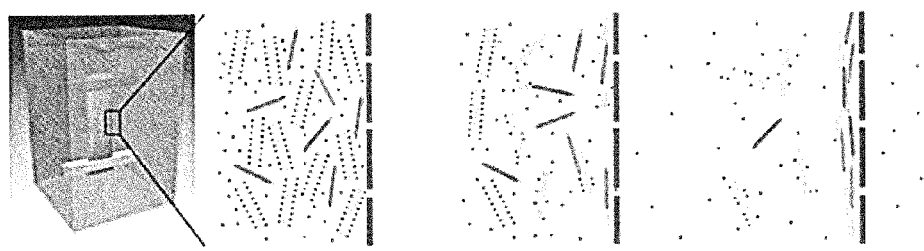
FIG. 1b schematically describes the principle on which a hybrid electronic sheet is formed according to an exemplary embodiment of the present disclosure.

The present disclosure also provides a method for preparing a hybrid electronic sheet including a graphitic material and a biomaterial capable of binding to the graphitic material, including: preparing a mixture by mixing a colloid material including a graphitic material with a biomaterial capable of binding to the graphitic material; and forming an electronic sheet in an aqueous solution by dialyzing the mixture using a membrane. FIG. 1a schematically describes the preparation method according to the present disclosure and FIG. 1b describes the principle on which the hybrid electronic sheet is formed.

In an exemplary embodiment, the colloid material is specifically an aqueous solution wherein a graphitic material is dispersed or dissolved. The colloid material may be prepared, before preparing the mixture, by adding a graphitic material to a solution containing a surfactant and stabilizing the same. The surfactant may be, for example, sodium cholate but is not limited thereto as long as it can stabilize a graphitic material and is biocompatible with a biomaterial.

In an exemplary embodiment, the graphitic material is not specially limited as long as it is a carbon nanomaterial. For example, it may be one or more selected from a group consisting of a graphene sheet, a highly oriented pyrolytic graphite (HOPG) sheet, a carbon nanotube such as a single-walled carbon nanotube, a double-walled carbon nanotube, a multi-walled carbon nanotube, etc. and fullerene. The graphitic material may be a metallic, semiconductor or hybrid material. More specifically, the graphitic material may be a mixture of a graphene sheet and a single-walled carbon nanotube.

For example, when a graphene sheet is used as the graphitic material, the 2-dimensional structure of the graphene sheet allows a larger contact area between constituent materials as compared to a material of 1-dimensional structure. Therefore, a hybrid electronic sheet of a larger area can be realized. And, when a mixture of a graphene sheet and a single-walled carbon nanotube is used as the graphitic material, the problem that a high concentration is necessary only when the graphene sheet is used can be solved while providing the advantage of the 2-dimensional structure of the graphene sheet. In addition, when a graphene sheet is mixed with a single-walled carbon nanotube, the size and thickness of the sheet become larger and, in this case, the effective area of a nanoelectrode per unit area is large. Therefore, the applicability as a flexible electrode is high.

In an exemplary embodiment, the biomaterial is a material capable of specifically and strongly binding to the graphitic material, in a nondestructive manner. For example, the biomaterial may be an M13 phage genetically modified to be capable of binding to the graphitic material. Specifically, the M13 phage genetically modified to be capable of binding to the graphitic material as an exemplary embodiment of the biomaterial may be one in which a peptide including one or more amino acid sequence selected from DSWAADIP (SEQ ID NO 1) and DNPIQAVP (SEQ ID NO 2) is displayed. The peptide may be displayed on the coat protein P3, P6, P7, P8 or P9 of the M13 phage. Among them, p3, p6, p7 and p9 are minor coat proteins and p8 is a major coat protein. The major coat protein p8 is advantageous in that, whereas the minor coat proteins have a very small copy number of 5 or smaller, it has a very large copy number of 2700 and provides a relatively very larger area for peptide display since it is located at the body of the phage. Accordingly, in an exemplary embodiment of the present disclosure, when a peptide of the present disclosure is displayed on the coat protein p8 located at the body of the M13 phage, the body of the phage itself, which is micrometers long (length: 880 nm, diameter ≤6.5 nm), may be used.

In an exemplary embodiment, the phage in which the peptide including one or more amino acid sequence selected from DSWAADIP (SEQ ID NO 1) and DNPIQAVP (SEQ ID NO 2) is displayed may be prepared by preparing an M13 phage display P8 peptide library and screening the same by binding it to a graphitic surface through biopanning. Alternatively, in another exemplary embodiment, it may be prepared directly through genetic recombination by introducing the peptide including one or more amino acid sequence selected from DSWAADIP (SEQ ID NO 1) and DNPIQAVP (SEQ ID NO 2) into the M13 phage itself.

In an exemplary embodiment, the mixing ratio of the colloid material and the biomaterial when preparing the mixture may be controlled as desired depending on the use of the electronic sheet. That is to say, it may be controlled depending on the desired properties of the electronic sheet, such as electrical conductivity, electrochemical charging current, hydrophilicity, etc. Further, the mixing ratio of the colloid material and the biomaterial may be controlled differently depending on the kind of the mixed biomaterial. For example, if the biomaterial is an M13 phage genetically modified to be capable of binding to the graphitic material, the colloid material and the biomaterial may be mixed with a molar ratio of from 20:1 to 1:30, more specifically from 20:1 to 1:20. More specifically, when the colloid material and the M13 phage genetically modified to be capable of binding to the graphitic material are mixed with a molar ratio of 4:1, the charging current of the electronic sheet may be improved greatly to 4 times or more as compared to a Au film. In this case, the electronic sheet may be usefully used as a flexible biosensor electrode, a brain surface electrode, an electrode for a flexible battery or a supercapacitor, etc.

Further, network formation of the graphitic material in the hybrid electronic sheet may be controlled by controlling the molar ratio of the colloid material and the biomaterial. In case of a hybrid single-walled carbon nanotube which is not electrically isolated, semiconductor property may be achieved by controlling the molar ratio of the graphitic material and the biomaterial. For example, when the hybrid single-walled carbon nanotube as the graphitic material and the M13 phage genetically modified to be capable of binding to the graphitic material are mixed with a molar ratio of 1:8, the hybrid electronic sheet may exhibit a p-type semiconductor property and thus can be used to prepare an active device. That is to say, a semiconductor or metallic hybrid electronic sheet can be obtained by controlling the molar ratio of the graphitic material and the biomaterial and, accordingly, a flexible electronic device or a transparent, flexible electronic device can be realized not only on a flat substrate but also on a non-conventional substrate.

If the molar ratio of the colloid material and the M13 phage genetically modified to be capable of binding to the graphitic material exceeds 20:1, formation of a large-area electronic sheet may be difficult due to decreased structural stability of the electronic sheet. And, if the molar ratio is lower than 1:30, application as an electrode may be difficult because the electrical resistance of the electronic sheet increases greatly. When the molar ratio is in the range between 20:1 and 1:30, a hybrid electronic sheet exhibiting superior electrical property and stable structural property may be formed.

In the method for preparing an electronic sheet according to the present disclosure, the step of forming the electronic sheet by dialyzing may include dialyzing a membrane tube to which the mixture has been added using the dialysis solution or dialyzing the mixture using the membrane itself. The membrane is not limited in shape or property as long as it is a semipermeable membrane capable of dialyzing the mixture. For example, in an exemplary embodiment, the step of forming the electronic sheet by dialyzing may include: adding an ion to a dialysis solution; adding the resulting mixture to a membrane tube; and dialyzing the membrane tube to which the mixture has been added using the dialysis solution to which the ion has been added. And, the dialysis solution may be distilled water, more specifically triply distilled water (resistance >18 MΩ cm), when considering the stability of the biomaterial included in the mixture.

Figure 2A:
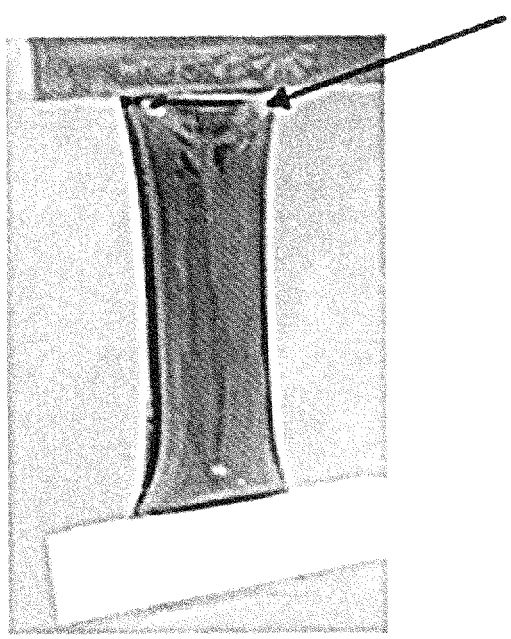
FIG. 2a shows an image of a hybrid electronic sheet formed according to an exemplary embodiment of the present disclosure.

Specifically, if the membrane tube containing the colloid material including the biomaterial and the graphitic material is dialyzed using distilled water for about 16-36 hours, a thin electronic sheet is formed along the surface of the membrane tube. FIG. 2a shows an image of the formed electronic sheet. The reason why such a thin electronic sheet is formed is as follows. While the dialysis proceeds, the concentration of the surfactant, which is attached on the surface of the graphitic material in the colloid material and stabilizes the carbonaceous material, in the tube decreases due to diffusion owing to the concentration difference inside and outside the membrane. This diffusion-driven dilution is the most prominent near the membrane. Since the biomaterial which exhibits strong binding ability to the graphitic material can begin reacting with the graphitic material only when the concentration of the surfactant surrounding the graphitic material is low, the binding occurs near the membrane where the dilution occurs the most actively. Based on this principle, a sheet may be formed through dialysis.

The concentration of the ion in the dialysis solution is more than or equal to 0 mM and less than 10 mM. The concentration of the ion can be controlled by adding a monovalent electrolyte to the dialysis solution. For example, 0.1 mM NaCl may be added to triply distilled water as the dialysis solution.

Figure 2B:
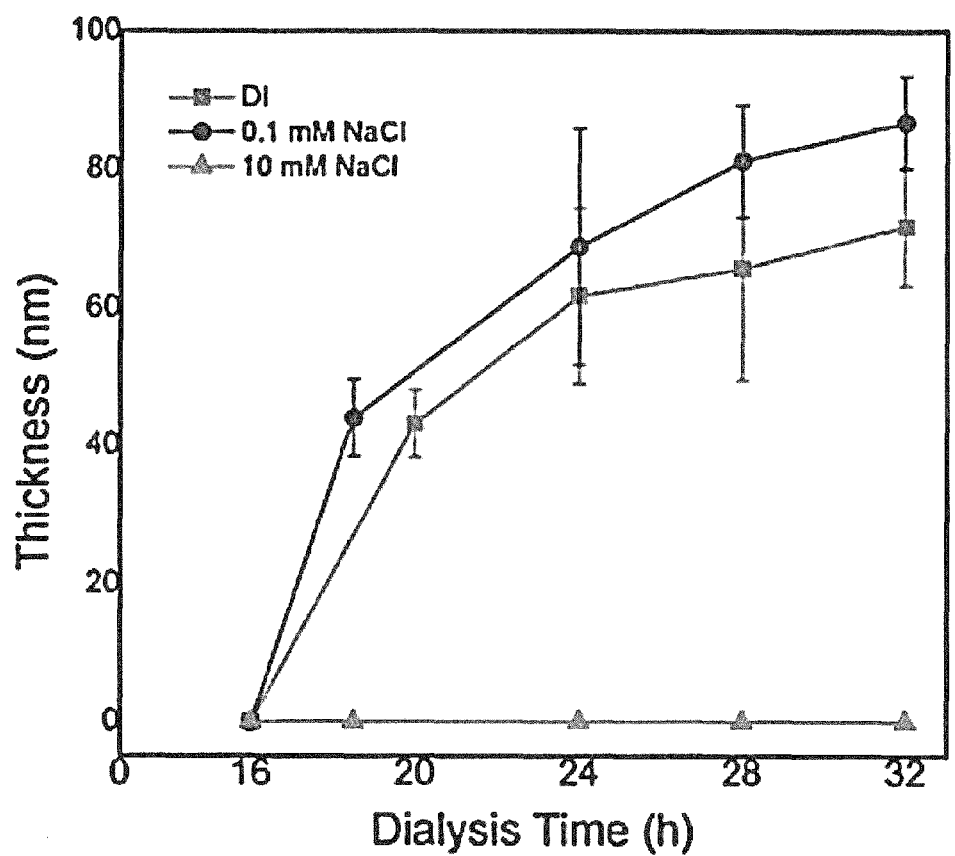
FIG. 2b shows the dependency of electronic sheet formation on the ionic strength of a dialysis solution according to an exemplary embodiment of the present disclosure.

To form a sheet-type hybrid electronic material, i.e. a hybrid electronic sheet, through dialysis, it is important to form binding between the graphitic material and the biomaterial mostly along the membrane of the membrane tube. In this regard, the ionic strength (i.e., ion concentration) of the distilled water is a very important factor. If the ionic strength of the distilled water satisfies the above range, continuous sheet formation is possible since the graphitic material remains dispersed well in the membrane tube while the sheet is formed through strong binding between the graphitic material which is negatively (−) charged owing to the adsorbed surfactant and thus exhibits strong electrical repulsion and the biomaterial along the membrane. In contrast, if the ionic strength is higher than the above range, aggregation may occur between the graphitic materials in the membrane because of decreased stabilization by the surfactant adsorbed on the graphitic material and, in an extreme case, only severe aggregation may occur in the tube without sheet formation. FIG. 2b shows the dependency of electronic sheet formation on the ionic strength of the distilled water. Referring to FIG. 2b, an electronic sheet is formed normally when the ion concentration of the distilled water is 0 (DI) or 0.1 mM, but an electronic sheet is not formed when the ion concentration of the distilled water is 10 mM (sheet thickness=0). The molar ratio of SWNT:p8 GB#1 is 4:1.

Figure 3A:
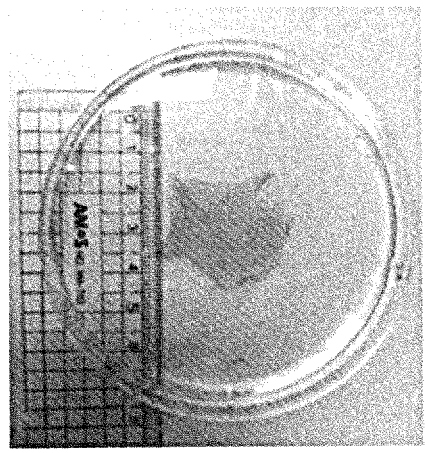
FIG. 3a shows an image of a large-area freestanding hybrid electronic sheet according to an exemplary embodiment of the present disclosure.
Figure 3B:
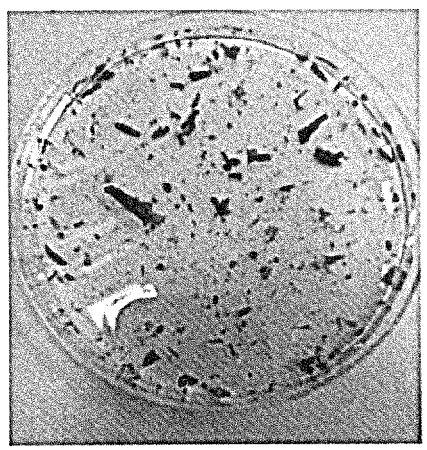
FIG. 3b shows an image of a sample prepared using a single-walled carbon nanotube without a phage as a comparison to the present disclosure.

In an exemplary embodiment, the preparation method according to the present disclosure may further include, after said forming the electronic sheet by dialyzing, separating the formed electronic sheet in an aqueous solution. The separation may be accomplished, for example, by twisting the membrane tube used for the dialysis to separate the electronic sheet formed along the membrane. A freestanding electronic sheet can be easily obtained by controlling the membrane clip in an aqueous solution. FIG. 3a shows an image of a freestanding electronic sheet prepared and separated according to an exemplary embodiment of the present disclosure. The prepared and separated freestanding electronic sheet maintains its shape through strong binding between the graphitic material and the biomaterial. If dialysis is conducted without adding the biomaterial, an electronic sheet is formed near the membrane but is limited in application because it is brittle. FIG. 3b shows an image of an electronic sheet prepared by dialysis without using a biomaterial. To compare FIG. 3a and FIG. 3b, it can be seen that, whereas the electronic sheet of FIG. 3a prepared using a biomaterial is formed stably with a large area due to the binding between the graphitic material and the biomaterial, the electronic sheet of FIG. 3b prepared without a biomaterial is broken into pieces during the preparation process. In addition, since the formation of the electronic sheet simply depends on the aggregation of the graphitic material by a dilution effect, a microstructure with severe bundling is obtained. In contrast, when a biomaterial is used as in the exemplary embodiment of the present disclosure, a nanostructure wherein the graphitic material is uniformly dispersed is obtained due to the binding of the graphitic material with the biomaterial. As a result, a large-area, ultra-flexible electronic sheet having a thickness of 350 nm or smaller and an area of tens of $cm^2$ can be prepared. For example, the electronic sheet prepared according to an exemplary embodiment of the present disclosure may have an area of 0.0001-1000 $cm^2$, 0.0001-100 $cm^2$, more specifically 1-20 $cm^2$, and a thickness of 40-350 nm. However, the size of the electronic sheet produced according to the method of the present disclosure is not specially limited. The produced electronic sheet may be torn during detachment or transfer. The tendency of tearing is less for an electronic sheet having a larger thickness (about 350 nm). If the concentration of the mixture is increased to increase thickness, aggregation may occur and a nonuniform electronic sheet may be formed.

In an exemplary embodiment, the method for preparing an electronic sheet may further include replicating the separated hybrid electronic sheet in the aqueous solution using a suitable substrate or mask. The replicated and dried electronic sheet may be used for various materials and devices without chemical etching. In an exemplary embodiment, the present disclosure may provide an electronic device including the electronic sheet. The electronic device may include, for example, an information processing device, an information storing device, a biodevice such as a biosensor and a bioelectrode or an energy device.

Further, since the electronic sheet according to an exemplary embodiment of the present disclosure is transparent, it may be widely applied to applications requiring transparent electronic devices (see FIG. 6a).

In an exemplary embodiment, the preparation method according to the present disclosure may further include, before the step of preparing the mixture or after the step of forming the electronic sheet, functionalizing the biomaterial capable of binding to the graphitic material with an enzyme. In this case, since the electronic sheet includes a biomaterial capable of binding to the graphitic material and further functionalized with a biochemical enzyme, a nanohybrid enzyme electrode wherein the biochemical enzyme and a nanoelectrode material are effectively nanostructured may be provided. Accordingly, a high-performance flexible biosensor which is selective for an analyte and can operate without a mediator that helps electron transport between the enzyme and the electrode may be provided. In an exemplary embodiment of the present disclosure, the enzyme may be horseradish peroxidase (HRP). If the electronic sheet according to an exemplary embodiment of the present disclosure is functionalized with HRP, the electronic sheet reacts selectively with hydrogen peroxide since HRP is an enzyme that reduces hydrogen peroxide ($H_2O_2$) to water ($H_2O$). In an exemplary embodiment, the step of functionalizing the biomaterial of the electronic sheet of the present disclosure with the enzyme may include, for example, conjugating the biomaterial with the enzyme, specifically using 1-ethyl-3-(3-dimethylaminopropyl)carbodiimide (EDC), N-hydroxysulfosuccinimide (sulfo-NHS) or glutaraldehyde.

The substrate or mask may be prepared from a metal, a semiconductor, an insulator, a polymer, an elastomer, etc. For example, a flexible electronic device may be prepared by replicating the electronic sheet using a flexible polymer substrate.

In an exemplary embodiment, a pattern may be formed on the electronic sheet by replicating the separated electronic sheet using a patterned substrate or mask. For example, if a patterned stencil mask is used, the pattern is formed on the electronic sheet when the mask is detached after the electronic sheet is completely dried. Accordingly, a device can be realized on a flexible electronic sheet without additional physical or chemical etching.

Hereinafter, the present disclosure will be described in detail through examples and test examples. However, the following examples test examples are for illustrative purposes only and it will be apparent to those of ordinary skill in the art that the scope of the present disclosure is not limited by the examples test examples.

Preparation Example 1

Preparation of Hybrid Electronic Sheet 1

As an exemplary embodiment of the present disclosure, a hybrid electronic sheet was prepared as follows.

Preparation of Colloid Solution

First, an aqueous solution was prepared by adding 2% w/v sodium cholate as a surfactant to distilled water and a colloid solution was prepared by stabilizing a single-walled carbon nanotube (SuperPure SWNT, solution type, 250 mg/mL, Nanointegris) as a graphitic material with the sodium cholate by dialyzing for 48 hours.

Assuming that the average length and the average diameter of the carbon nanotube (CNT) are 1 μm and 1.4 nm, respectively, the number of the single-walled carbon nanotube included in the colloid solution can be calculated according to the following equation.

Number of single-walled carbon nanotube (/mL)= concentration (μg/mL)×3×10$^{11}$      [Equation 1]

The number of the single-walled carbon nanotube included in the colloid solution was calculated as $7.5 \times 10^{13}$/mL.

Preparation of Biomaterial

An M13 phage in which the peptide DSWAADIP (SEQ ID NO 1) is displayed (p8 GB#1) and an M13 phage in which the peptide DNPIQAVP (SEQ ID NO 2) is displayed (p8 GB#5), wherein the peptides are capable of strongly binding to a graphitic surface, were prepared as follows.

First, an M13HK vector was prepared by site-directed mutating the 1381st base pair C of an M13KE vector (product # N0316S, SEQ ID NO 3, NEB) into G.

The M13KE vector (product # N0316S, NEB) is a cloning vector consisting of a 7222-bp DNA and its genetic information is available from the Internet (https://www.neb.com/-/media/NebUs/Page%20Images/Tools%20and%20Resources/Interactive%20Tools/DNA%20Sequences%20and%20Maps/Text%20Documents/m13kegbk.txt). The base sequences of oligonucleotides used for the site-directed mutagenesis are as follows:

```
                                        (SEQ ID NO 4)
5'-AAG GCC GCT TTT GCG GGA TCC TCA CCC TCA GCA GCG

AAA GA-3'.

(SEQ ID NO 5)
5'-TCT TTC GCT GCT GAG GGT GAG GAT CCC GCA AAA GCG

GCC TT-3'.
```

Phage display p8 peptide libraries were prepared from the M13HK vector using the restriction enzymes BspHI (product # R0517S, NEB) and BamHI (product # R3136T, NEB).

The base sequences of oligonucleotides used for the preparation of the phage display p8 peptide libraries are as follows:

```
                                        (SEQ ID NO 6)
5'-TTA ATG GAA ACT TCC TCA TGA AAA AGT CTT TAG TCC

TCA AAG CCT CTG TAG CCG TTG CTA CCC TCG TTC CGA TGC

TGT CTT TCG CTG CTG-3'.

(SEQ ID NO 7)
5'-AAG GCC GCT TTT GCG GGA TCC NNM NNM NNM NNM NNM

NNM NNM NCA GCA GCG AAA GAC AGC ATC GGA ACG AGG GTA

GCA ACG GCT ACA GAG GCT TT-3'.
```

The base sequences of the prepared phage display p8 peptide libraries have a diversity of $4.8 \times 10^7$ plaque-forming units (PFU) and each sequence has a copy number of about $1.3 \times 10^5$.

Then, the prepared phage display p8 peptide libraries were bound to a graphitic surface by biopanning so as to screen the phage in which the peptide as the biomaterial according to the present disclosure is displayed. Specifically, the biopanning was conducted as follows.

First, a fresh surface was detached from a highly oriented pyrolytic graphite (HOPG, product #439HP-AB, SPI) as a material having a graphitic surface using a tape to minimize defects due to, e.g., oxidation of the sample surface. A HOPG substrate with a relatively large grain size of 100 μm or smaller was used.

Then, the prepared $4.8 \times 10^{10}$ ($4.8 \times 10^7$ diversities, 1000 copies per each sequence) phage display p8 peptide libraries were prepared in 100 μL of Tris-buffered saline (TBS) and conjugated with the HOPG surface in a shaking incubator for 1 hour at 100 rpm. 1 hour later, the solution was removed and the HOPG surface was washed 10 times with TBS. The washed HOPG surface was reacted with pH 2.2 Tris-HCl as an acidic buffer for 8 minutes to elute the non-selectively reacting peptide and then XL-1 blue *E. coli* culture in mid-log state was eluted for 30 minutes. A part of the eluted culture was left for DNA sequencing and peptide identification and the remainder was amplified to prepare sub-libraries for the next round. The above procedure was repeated using the prepared sub-libraries. The left plaques were subjected to DNA analysis to identify the p8 peptide sequence. As a result, a phage in which the peptide DSWAADIP (SEQ ID NO 1) is displayed (p8 GB#1) and a phage in which the peptide DNPIQAVP (SEQ ID NO 2) is displayed (p8 GB#5), wherein the peptides are capable of strongly binding to a graphitic surface, were obtained.

Preparation of Hybrid Electronic Sheet

The colloid solution prepared above and a phage solution containing the M13 phage (p8 GB#1) capable of strongly binding to a graphitic surface were mixed with a molar ratio of 4:1 (Example 1), 10:1 (Example 2), 20:1 (Example 3), 1:2 (Example 4), 1:4 (Example 5) or 1:8 (Example 6).

Next, each of the mixtures was added to a semipermeable dialysis membrane tube (MWCO 12,000-14,000, product #132 700, SpectrumLab) and each membrane tube was dialyzed using triply distilled water. About 16 hours after the dialysis was started, a thin electronic sheet was formed along the surface of the membrane tube. FIG. 2a shows an image of the formed electronic sheet of Example 1.

Next, each membrane tube was transferred to triply distilled water and the electronic sheet was detached by twisting the membrane of the membrane tube and then dried. FIG. 3a shows an image of the detached electronic sheet of Example 1. The prepared electronic sheet of Example 1 had a thickness of about 100 nm.

Preparation Example 2

Preparation of Hybrid Electronic Sheet 2

As another exemplary embodiment of the present disclosure, a hybrid electronic sheet was prepared in the same manner as in Preparation Example 1 except that the biomaterial was prepared by genetic recombination as follows.

Preparation of Biomaterial

M13HK was prepared directly by genetic recombination using the restriction enzymes BspHI (product # R0517S, NEB) and BamHI (product # R3136T, NEB). The base sequences used to prepare the M13 phage in which the peptide DSWAADIP (SEQ ID NO 1) is displayed on the body (p8 GB#1) were as follows.

```
                                                   (SEQ ID NO 8)
5' [Phos] CATGAAA AAGTCTTTTG TCCTCAAAGC

CTCTGTAGCC GTTGCTACCC TCGTTCCGAT GCTGTCTTTC

GCTGCTGATT CTTGGGCTGC GGATATTCCG 3'.

(SEQ ID NO 9)
5' [Phos] GATC CGGAATATCC GCAGCCCAAG AATCAGGCAGC

GAAAGACAGC ATCGGAACGA GGGTAGCAAC GGCTACAGAG

GCTTTGAGGA CAAAGACTT TTT 3'.
```

The base sequences used to prepare the M13 phage in which the peptide DNPIQAVP (SEQ ID NO 2) is displayed on the body (p8 GB#5) were as follows.

```
                                                   (SEQ ID NO 10)
5' [Phos] CATGAAA AAGTCTTTTG TCCTCAAAGC

CTCTGTAGCC GTTGCTACCC TCGTTCCGAT GCTGTCTTTC

GCTGCTGATA ATCCGATTCA GGCTGTTCCG 3'.

(SEQ ID NO 11)
5' [Phos] GATC CGGAACAGCC TGAATCGGAT TATCAGGCAGC

GAAAGACAGC ATCGGAACGA GGGTAGCAAC GGCTACAGAG

GCTTTGAGGA CAAAGACTT TTT 3'.
```

The DNAs of SEQ ID NOS 8 and 9 were annealed at 95° C. for 2 minutes and cooled to 25° C. at a rate of 0.1° C./s. Then, the M13HK vector digested with the restriction enzymes BspHI and BamHI (after reaction with the enzymes at 37° C. for 2 hours, the enzymes were inactivated at 65° C. for 20 minutes) and then reacted T4 DNA ligase (product # M0202S, NEB) at 16° C. for 12 hours to obtain a circular vector. The ligated circular DNA was inserted into electro-competent *E. coli* (XL-1 Blue cell line, product #200228, Agilent) through electroporation and genetically recombined M13 phage was amplified by culturing in a shaking incubator at 37° C. for 6 hours (following the instruction of the product manual for product #200228, Agilent). In order to purify the phage from the culture wherein the phage and *E. coli* are mixed, the culture medium was centrifuged at 8000 rpm for 30 minutes and only the supernatant was taken. Since the phage was include in the supernatant, the separated supernatant was mixed with 20% w/v polyethylene glycol (molecular weight 8000, product # V3011, Promega Corporation)/NaCl solution, with a volume of ⅙ of that of the supernatant solution, and centrifuged at 12000 rpm for 30 minutes after reaction at 4° C. for about 16 hours. After discarding the supernatant from the resulting solution, the remaining phage was dissolved in Tris-buffered saline (TBS, product # S3001, Dako) to obtain a phage solution. The concentration of the phage solution was calculated according to Equation 2.

Phage concentration (viral particles/mL)=$1.6 \times 10^{16} \times$ O.D.$_{viral\ solution}$/7237   [Equation 2]

The obtained phage solution can be amplified repeatedly using *E. coli*. The phage was amplified using *E. coli* (XL-1 blue cell line) in early-log state (overnight culture diluted to ¹⁄₁₀₀). The amplified phage was purified in the same manner as described above.

Comparative Example 1

Preparation of Electronic Sheet

As a comparative example of the present disclosure, an electronic sheet not including a biomaterial was prepared as follows.

First, an aqueous solution was prepared by adding 2% w/v sodium cholate as a surfactant to distilled water and a colloid solution was prepared by stabilizing a single-walled carbon nanotube (SuperPure SWNT, solution type, 250 mg/mL, Nanointegris) as a graphitic material with the sodium cholate by dialyzing for 48 hours.

Next, 0.4 mL of the colloid solution diluted with 10 mL of 1% w/v sodium cholate aqueous solution was added to a semipermeable dialysis membrane tube (MWCO 12,000-14,000, product #132 700, SpectrumLab) and the membrane tube was dialyzed using triply distilled water.

About 24 hours after the dialysis was started, an electronic sheet was formed along the surface of the membrane tube. Next, the membrane tube was transferred to triply distilled water and the electronic sheet was detached by twisting the membrane of the membrane tube. FIG. 3*b* shows an image of the detached electronic sheet of Comparative Example 1.

Figure 4:
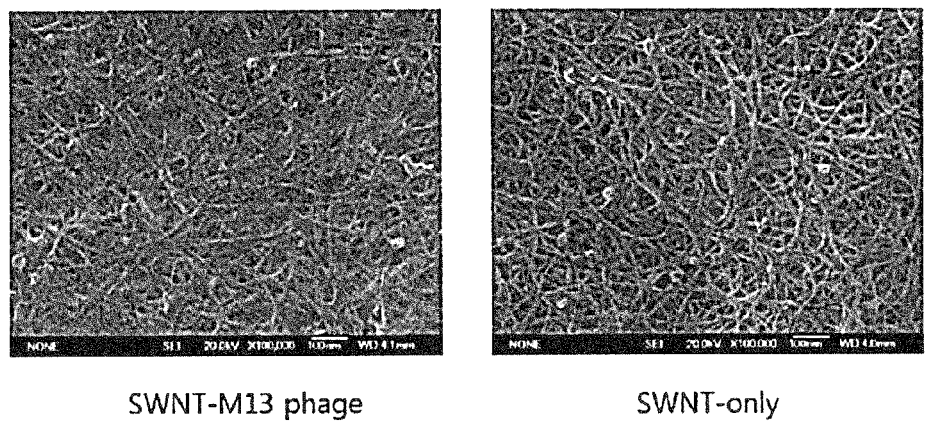
FIG. 4 shows scanning electron microscopic (SEM) images comparing the nanostructure of an electronic sheet according to an exemplary embodiment of the present disclosure (SWNT-M13 phage) and a comparative sample prepared using a single-walled carbon nanotube without a phage (SWNT-only).

FIG. 4 shows scanning electron microscopic (SEM) images comparing the nanostructure of the electronic sheets Example 1 (SWNT-M13 phage) and Comparative Example 1 (SWNT-only). As seen from FIG. 4, the electronic sheet of Comparative Example 1 (SWNT-only), which does not include a biomaterial, showed severe bundling due to aggregation of single-walled carbon nanotubes. In contrast, the electronic sheet of Example 1 (SWNT-M13 phage) had a nanostructure in which the biomaterial and the single-walled carbon nanotube are strongly bound and uniformly distributed.

Test Example 1

Figure 5A:
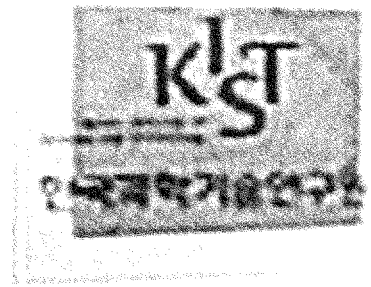
FIG. 5a shows an image of an electronic sheet according to an exemplary embodiment of the present disclosure transferred onto a PES polymer substrate.
Figure 5B:
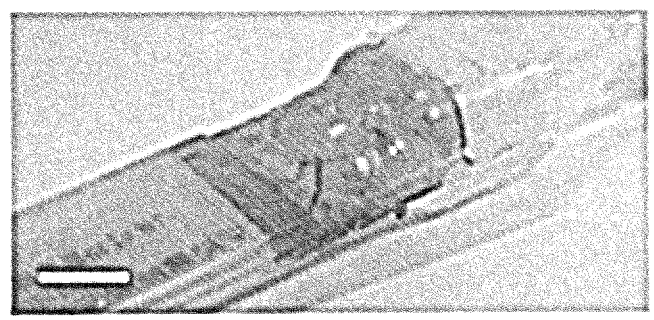
FIG. 5b shows an image of an electronic sheet according to an exemplary embodiment of the present disclosure transferred onto a plastic with a complex shape.
Figure 7:
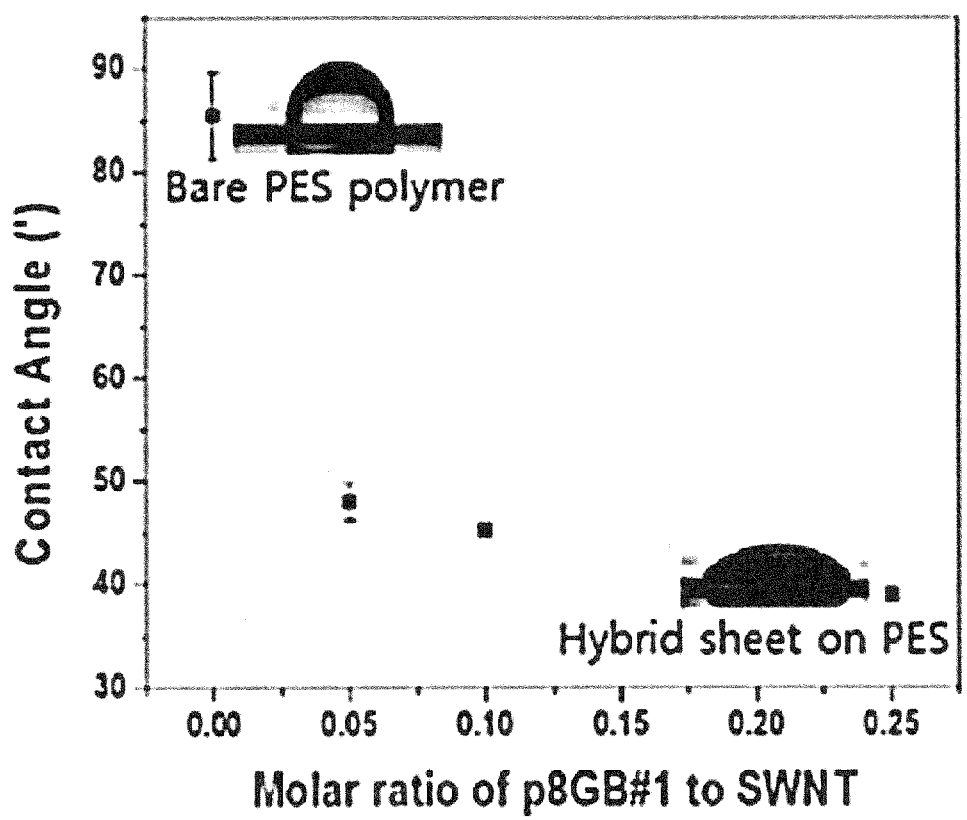
FIG. 7 shows a result of measuring contact angles to compare the change in hydrophilic property of an electronic sheet according to an exemplary embodiment of the present disclosure depending on the molar ratio of a graphitic material (SWNT) and a biomaterial (p8 GB#1) in the electronic sheet (SWNT:p8 GB#1=4:1, 10:1 or 20:1).

Comparison of Hydrophilicity of Electronic Sheet Depending on Mixing Ratio of Graphitic Material and Biomaterial The electronic sheets of Examples 1-3 prepared in Preparation Example 1 were transferred onto a polymer (polyethersulfone; PES) substrate (hybrid sheet on PES) and their hydrophilic property was compared with the electronic sheets of Examples 1-3 not transferred onto the polymer substrate (bare PES polymer). The result is shown in FIG. 7. FIG. 5*a* shows an image of the electronic sheet of Example 1 transferred onto the polymer substrate.

The hydrophilic property of the electronic sheets was compared by measuring contact angles since a large surface contact angle indicates stronger hydrophobicity and a smaller contact angle indicates stronger hydrophilicity. After dropping 20 mL of distilled water on the substrate onto which the electronic sheets of Examples 1-3 had been transferred, contact angles were measured 5 minutes later.

As seen from FIG. 7, the contact angle was about 2-3 times smaller when the electronic sheets of Examples 1-3 were transferred onto the polymer substrate (hybrid sheet on PES) than when the electronic sheets of Examples 1-3 were transferred (bare PES polymer). Accordingly, it can be seen that the electronic sheet according to the present disclosure has high hydrophilicity.

Test Example 2

Comparison of Electrochemical Property of Electronic Sheet

The electronic sheet of Example 1 prepared in Preparation Example 1 was transferred onto a polymer (PES) substrate and a gold (Au) film and their charging current (current density) was compared as follows.

The charging current was measured using a potentiostat/galvanostat (VersaStat 3, Princeton Applied Research (PAR)). Pt wire and Ag/AgCl (3 M KCl saturated, K0260, PAR) were used as a counter electrode (K0266, PAR) and a reference electrode, respectively, and phosphate-buffered saline (PBS; 0.1 M phosphate, pH=7.4) was used as an electrolyte. The measurement was made in a voltage range of 0-0.6 V at a scan rate of 250 mV/s. The result is shown in FIG. 8.

Figure 8:
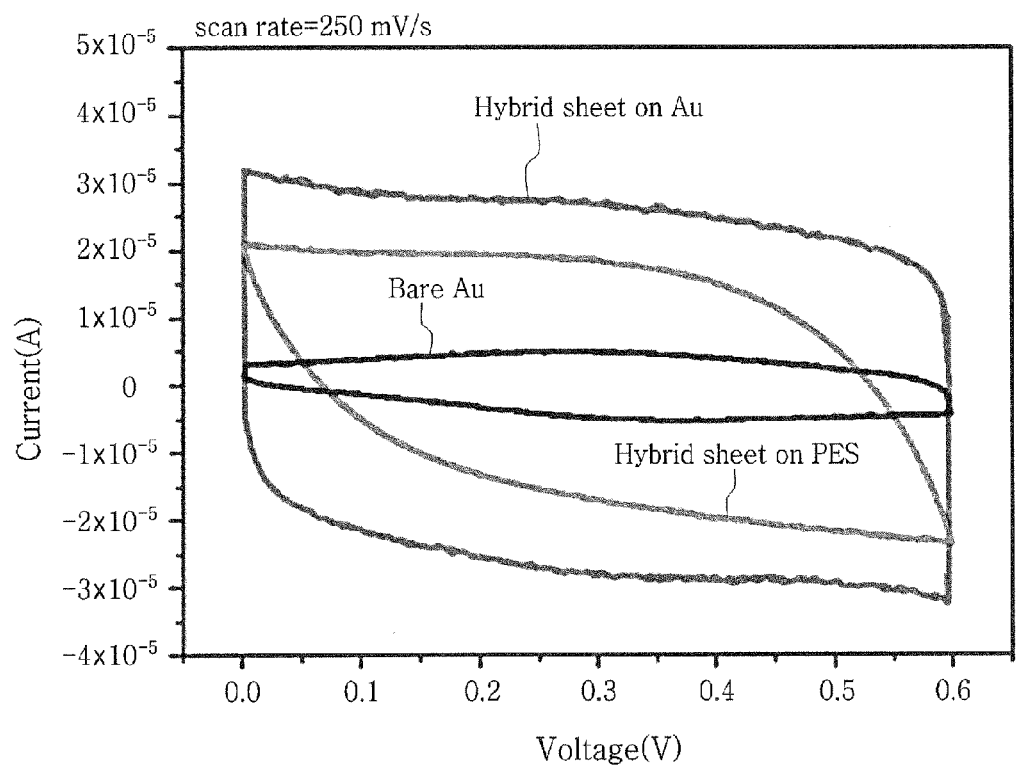
FIG. 8 shows a result of comparing the electrochemical conductivity (current and voltage) of an electronic sheet according to an exemplary embodiment of the present disclosure transferred onto a polymer or Au substrate (hybrid sheet on Au or hybrid sheet on PES) with that of a bare Au film (bare Au).

Since higher charging current for the same sample area indicates better conductivity and good formation of a nanostructure, it can be seen from FIG. 8 that the electronic sheet according to the present disclosure exhibits superior conductivity and has a well-defined nanostructure. In addition, the fact that the electronic sheet exhibits about 4 times higher charging current on a transparent insulating polymer substrate without a metal film (hybrid sheet on PES) than on a metal film (bare Au) shows that the electronic sheet can also be used for electrochemical electrodes which require not only flexibility but also transparency.

Test Example 3

Figure 9:
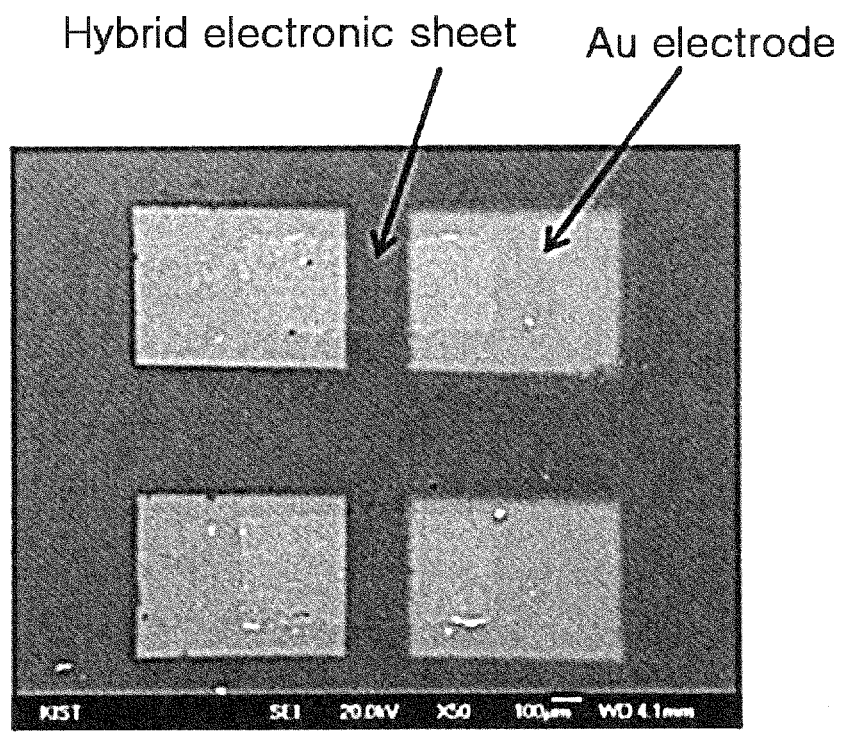
FIG. 9 shows an SEM image of an electronic device including an electronic sheet according to an exemplary embodiment of the present disclosure.

Comparison of Electrical Conductivity of Electronic Sheet Depending on Mixing Ratio of Graphitic Material and Biomaterial Patterns of the electronic sheets of Examples 4-6 prepared in Preparation Example 1 were formed on a $SiO_2$ (300 nm)/Si substrate (EPI-Prime Si wafer, Siltron Inc.) using a stencil mask. Then, a 100-nm Au electrode was formed as an electrode for measurement by sputtering using another stencil mask. FIG. 9 shows an SEM image of an electronic device prepared by transferring the electronic device of Example 4.

Figure 10:
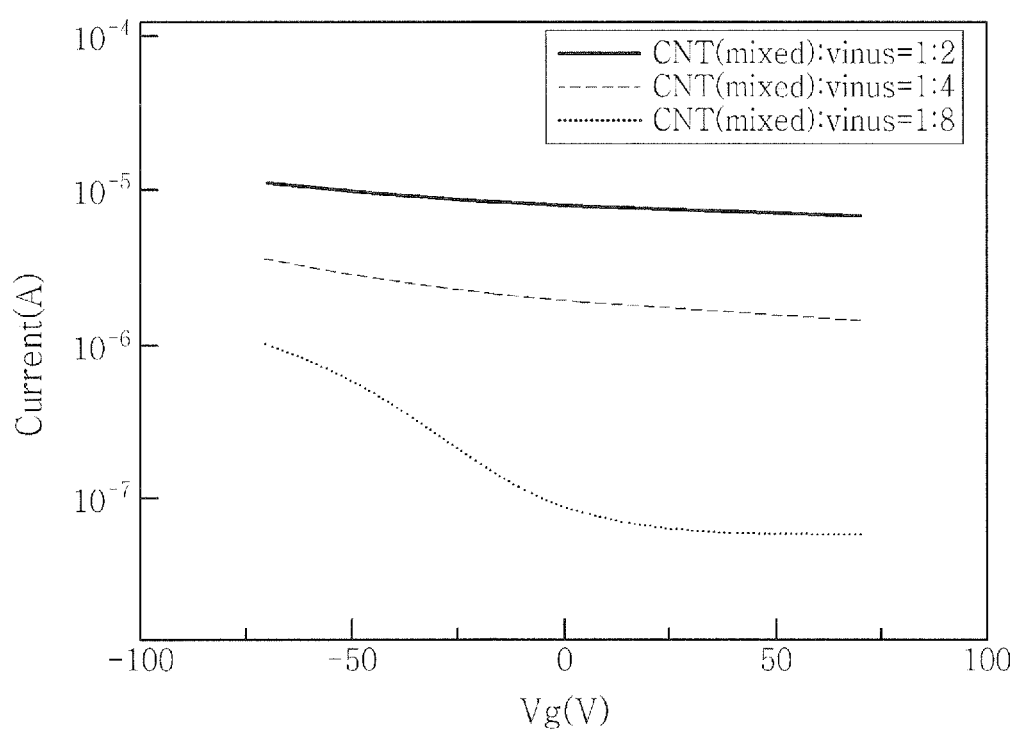
FIG. 10 shows a current-voltage (I-V) curve of an electronic sheet according to an exemplary embodiment of the present disclosure depending on the molar ratio of a graphitic material (SWNT) and a biomaterial (p8 GB#1) in the electronic sheet (SWNT:p8 GB#1=1:2, 1:4 or 1:8) and gate voltage.

FIG. 10 shows a current-voltage (I-V) curve of the electronic sheets as a function of applied back gate voltage. The electronic sheets exhibit p-type semiconductor properties because the current increased (i.e., resistance decreased) when the (−) gate voltage was applied. Also, better semiconductor property (on/off current ratio and off current) was exhibited as the molar ratio of the biomaterial increased. Since the hybrid single-walled carbon nanotube exhibited little tube bundling and semiconductor property near the threshold nanotube network density, it can be seen that the electrical conductivity of the electronic sheet can be controlled by controlling the mixing ratio of the graphitic material and the biomaterial. Accordingly, the electronic sheet of the present disclosure is applicable not only as an electrode but also as information processing and information storing devices.

Preparation Example 3

Preparation of Hybrid Electronic Sheet 3

As an exemplary embodiment of the present disclosure, a hybrid electronic sheet was prepared using a mixture of a graphene sheet and a single-walled carbon nanotube as a graphitic material as follows.

Preparation of Colloid Solution

First, an aqueous solution was prepared by adding 2% w/v sodium cholate as a surfactant to distilled water and a colloid solution was prepared by stabilizing a single-walled carbon nanotube (SuperPure SWNT, solution type, 250 mg/mL, Nanointegris) and a graphene sheet (PureSheets QUATTRO, solution type, 50 mg/mL, Nanointegris) as graphitic materials with the sodium cholate by dialyzing for 48 hours.

Assuming that the average length and the average diameter of the carbon nanotube (CNT) are 1 μm and 1.4 nm, respectively, the number of the single-walled carbon nanotube included in the colloid solution is calculated as $7.5 \times 10^{13}$/mL according to Equation 1.

The number of the graphene sheet can be calculated as follows.

(1) It is assumed that, since the graphene sheet (Puresheets QUATTRO, Nanointegris) is composed of single layers (6%), double layers (23%), triple layers (27%) and quadruple layers (44%), it is 3.09 layers on average.

(2) Since the area of the graphene unit lattice is about 0.0524 $nm^2$ and there are two carbon atoms per lattice, the area occupied by one carbon atom is 0.0262 $nm^2$.

(3) Since each graphene sheet has an average area of 10,000 $nm^2$, there are $(10,000\ nm^2/0.0262\ nm^2) \times 3.09 = 1.18 \times 10^6$ carbon atoms per graphene sheet.

(4) The average weight of a graphene sheet is $\{1.18 \times 10^6/(6.02 \times 10^{23}\ mol^{-1}) \times 12\ g/mol = 2.35 \times 10^{-17}\ g$. Accordingly, the number of graphene sheets per 1 mg is $1 \times 10^{-6}\ g/2.35 \times 10^{-17}\ g = 4.3 \times 10^{10}$.

The following equation can be derived from above.

$$\text{Number of graphene nanotube (/mL)} = \text{concentration (μg/mL)} \times 4.3 \times 10^{10} \quad \text{[Equation 3]}$$

Since the concentration of the graphene sheet (Puresheets QUATTRO) solution was 50 μg/mL, it can be assumed that 1 mL of the solution contain $(50 \times 10^{-6}\ g)/(2.35 \times 10^{-17}\ g)\ 2.13 \times 10^{12}$ graphene sheets.

Preparation of Hybrid Electronic Sheet

The colloid solution prepared above and a phage solution containing the M13 phage (p8 GB#1) capable of strongly binding to a graphitic surface of Preparation Example 1 were mixed with a molar ratio of SWNT:graphene:p8 GB#1=10:2:1.

Next, each of the mixtures was added to a semipermeable dialysis membrane tube (MWCO 12,000-14,000, product #132 700, SpectrumLab) and each membrane tube was dialyzed using triply distilled water.

About 24 hours after the dialysis was started, a thin electronic sheet was formed along the surface of the membrane tube. Each membrane tube was transferred to triply distilled water and the electronic sheet was detached by twisting the membrane of the membrane tube and then dried. The prepared electronic sheet had a thickness of about 230 nm.

Figure 11:
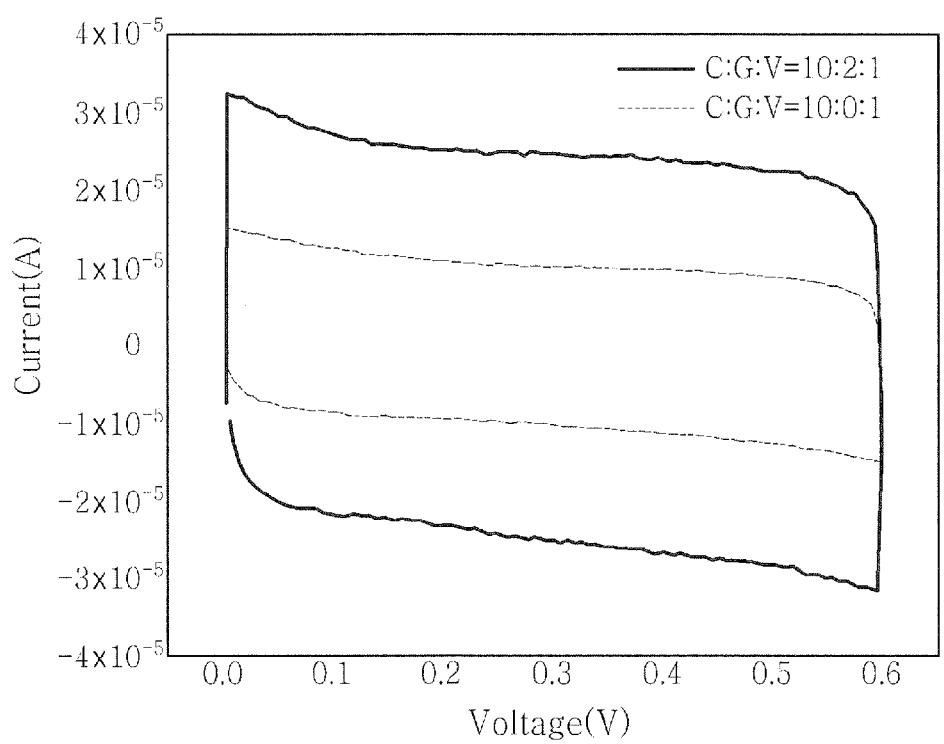
FIG. 11 shows a result of comparing the electrochemical conductivity of a hybrid electronic sheet according to an exemplary embodiment of the present disclosure wherein a single-walled carbon nanotube and graphene are mixed (C:G:V=10:2:1) with one wherein only a single-walled carbon nanotube is present (C:G:V=10:0:1) (C: single-walled carbon nanotube, G: graphene, V: p8 GB#1).

When compared with the electronic sheet of Example 2, which was prepared using a colloid solution containing only the single-walled carbon nanotube without graphene (C:G:V=10:0:1), the addition of graphene (C:G:V=10:2:1) resulted in increased sheet thickness and increased charging current per unit area (FIG. 11).

Preparation Example 4

Preparation of Hybrid Enzyme Electronic Sheet Functionalized with Biochemical Enzyme As an exemplary embodiment of the present disclosure, a hybrid enzyme electronic sheet including a biochemical enzyme and a nanoelectrode material was prepared as follows and a biosensor electrode which is selective for an analyte and can operate without a mediator that helps electron transport between the enzyme and the electrode was prepared using the same.

Preparation of Colloid Solution

First, an aqueous solution was prepared by adding 2% w/v sodium cholate as a surfactant to distilled water and a colloid solution was prepared by stabilizing a single-walled carbon nanotube (SuperPure SWNT, solution type, 250 mg/mL, Nanointegris) as a graphitic material with the sodium cholate by dialyzing for 48 hours.

Assuming that the average length and the average diameter of the carbon nanotube (CNT) are 1 μm and 1.4 nm, respectively, the number of the single-walled carbon nanotube included in the colloid solution is calculated as $7.5 \times 10^{13}$/mL according to Equation 1.

Preparation of HRP-p8 GB#1 Conjugate Wherein p8 GB#1 Phage is Functionalized with Horseradish Peroxidase (HRP)

The phage surface was functionalized with the enzyme HRP (product # P8375-5KU, Sigma-Aldrich) using 1-ethyl-3-(3-dimethylaminopropyl)carbodiimide (EDC) and N-hydroxysulfosuccinimide (sulfo-NHS). 4 mg of EDC (product # E1769, Sigma-Aldrich), 11 mg of sulfo-NHS (product #56485, Sigma-Aldrich) and 1 mg of P8 GB#1 were mixed in 0.5 mL of 0.1 mM MES buffer (pH 6.0, Sigma-Aldrich) and reacted at room temperature for 30 minutes under mild shaking. Then, 1.4 μL of 2-mercaptoethanol (2ME; product #35602, Pierce) was added to stop the EDC reaction. Subsequently, after adding 0.5 mL of 0.1 M phosphate-buffered saline (PBS, pH 7.2) solution in which 1 mg of HRP was dissolved, the mixture was reacted overnight. Then, the reaction was stopped by adding hydroxylamine (product #26103, Pierce) to a final concentration of 10 mM. The HRP-functionalized p8 GB#1 phage, i.e., HRP-p8 GB#1 conjugate, was purified using PEG/NaCl as described in Preparation Example 1.

Preparation of Hybrid Enzyme Electronic Sheet Functionalized with Biochemical Enzyme The prepared colloid solution and a solution containing the prepared HRP-p8 GB#1 were mixed at a molar ratio of 2:1. Then, the mixture was added to a semipermeable dialysis membrane tube (MWCO 12,000-14,000, product #132 700, SpectrumLab) and the membrane tube was dialyzed using triply distilled water with an ionic strength of 0.1 mM.

About 16 hours after the dialysis was started, a thin electronic sheet was formed along the surface of the membrane tube. The formed membrane tube was transferred to triply distilled water with an ionic strength of 0.1 mM and a freestanding hybrid enzyme electronic sheet was prepared by twisting the membrane of the membrane tube.

Test Example 4

Selective Current Biosensor without Electron Mediator

Figure 12A:
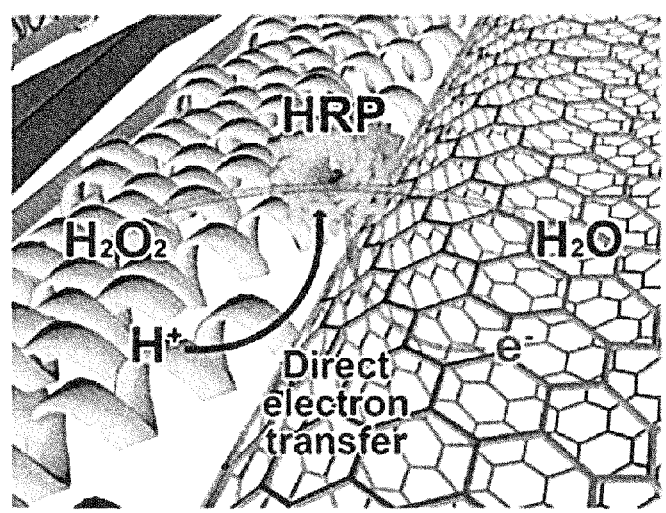
FIG. 12a schematically describes current biosensing using a hybrid enzyme electronic sheet functionalized with an enzyme according to an exemplary embodiment of the present disclosure.
Figure 12B:
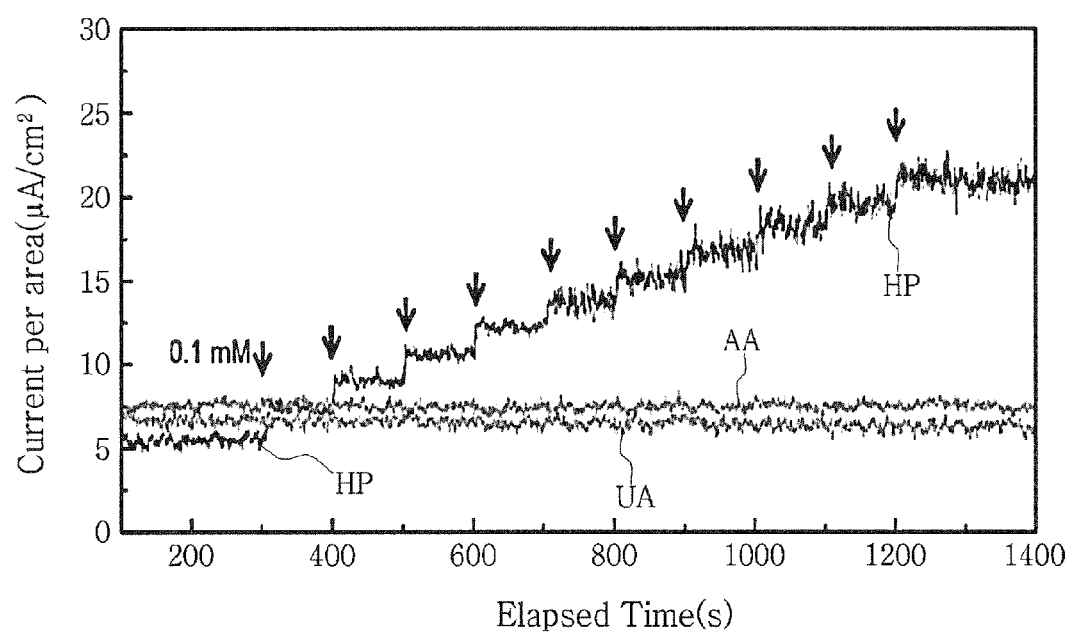
FIG. 12b shows selective current response of a hybrid enzyme electronic sheet functionalized with horseradish peroxidase (HRP) according to an exemplary embodiment of the present disclosure to hydrogen peroxide.

The prepared freestanding hybrid enzyme electronic sheet was transferred onto a Au substrate and hydrogen peroxide was detected by current biosensing. HRP is an enzyme which reduces hydrogen peroxide ($H_2O_2$) to water ($H_2O$) and reacts selectively with hydrogen peroxide. Since the reduction occurs only when the enzyme receives an electron, the measured reduction current is proportional to the amount of hydrogen peroxide (see FIG. 12a). The biosensing was conducted using the enzyme electronic sheet as a working electrode and using Pt wire and Ag/AgCl (3M KCl saturated, K0260, PAR) respectively as a counter electrode (K0266, PAR) and a reference electrode. Phosphate-buffered saline (PBS; 0.1 M phosphate, pH=7.4) was used as an electrolyte. The measurement was made at a voltage fixed to −200 mV. Current was measured while injecting the analyte with 100-second intervals to a final concentration of 0.1 mM. As seen from FIG. 12b, the enzyme electronic sheet functionalized with HRP responds only to hydrogen peroxide and does not respond to ascorbic acid or uric acid, which are widely known as interfering factors in current biosensing. Hydrogen peroxide could be detected effectively without using a mediator commonly used to improve the electron transport efficiency between the enzyme and the electrode. Accordingly, it was clearly demonstrated that the enzyme electronic sheet according to the present disclosure not only exhibits very superior selectivity but also can be used as an electrode of a high-performance current biosensor since the enzyme functionalized on the biomaterial surface and the carbon nanotube nanoelectrode exchange electrons directly. Also, a multienzyme electronic sheet functionalized with other biochemical enzymes whose product is hydrogen peroxide may be realized. For example, GOx-HRP-p8 GB#1, prepared by further functionalizing HRP-p8 GB#1 with glucose oxidase which oxidizes glucose to hydrogen peroxide, may be used to detect glucose by current biosensing. Accordingly, a flexible current glucose biosensor may be realized. In addition, a biosensor may also be prepared by selectively functionalizing the surface of the biomaterial in the hybrid electronic sheet formed in Preparation Example 1 or 2 with an enzyme.

What is claimed is:

1. A method for preparing a hybrid electronic sheet comprising a graphitic material and a biomaterial capable of binding to the graphitic material, comprising:

preparing a mixture by mixing a colloid material comprising a graphitic material with a biomaterial capable of binding to the graphitic material; and forming an electronic sheet in an aqueous solution by dialyzing the mixture using a membrane.

2. The method for preparing a hybrid electronic sheet according to claim 1, wherein the colloid material is an aqueous solution wherein a graphitic material is dispersed or dissolved.

3. The method for preparing a hybrid electronic sheet according to claim 1, which further comprises, before said preparing the mixture, preparing a colloid material by adding a graphitic material to a solution comprising a surfactant and stabilizing the same.

4. The method for preparing a hybrid electronic sheet according to claim 1, wherein said forming the electronic sheet by dialyzing comprises:
adding an ion to a dialysis solution;
adding the resulting mixture to a membrane tube; and
dialyzing the membrane tube to which the mixture has been added using the dialysis solution to which the ion has been added.

5. The method for preparing a hybrid electronic sheet according to claim 4, wherein the concentration of the ion in the dialysis solution to which the ion has been added is more than or equal to 0 mM and less than 10 mM.

6. The method for preparing a hybrid electronic sheet according to claim 1, which further comprises, before said preparing the mixture or after said forming the electronic sheet, functionalizing the biomaterial capable of binding to the graphitic material with an enzyme.

7. The method for preparing a hybrid electronic sheet according to claim 1, which further comprises, after said forming the electronic sheet by dialyzing, separating the formed electronic sheet in an aqueous solution.

8. The method for preparing a hybrid electronic sheet according to claim 7, which further comprises forming a pattern of the electronic sheet by replicating the separated electronic sheet using a patterned substrate or mask.

* * * * *

SEQUENCE LISTING

```
<160> NUMBER OF SEQ ID NOS: 11

<210> SEQ ID NO 1
<211> LENGTH: 8
<212> TYPE: PRT
<213> ORGANISM: Artificial Sequence
<220> FEATURE:
<223> OTHER INFORMATION: P8GB#1 which is a peptide having superior
      binding affinity for graphitic material

<400> SEQUENCE: 1

Asp Ser Trp Ala Ala Asp Ile Pro
1               5

<210> SEQ ID NO 2
<211> LENGTH: 8
<212> TYPE: PRT
<213> ORGANISM: Artificial Sequence
<220> FEATURE:
<223> OTHER INFORMATION: P8GB#5 which is a peptide having superior
      binding affinity for graphitic material
```

-continued

```
<400> SEQUENCE: 2

Asp Asn Pro Ile Gln Ala Val Pro
1               5

<210> SEQ ID NO 3
<211> LENGTH: 7222
<212> TYPE: DNA
<213> ORGANISM: Artificial Sequence
<220> FEATURE:
<223> OTHER INFORMATION: cloning vector M13KE

<400> SEQUENCE: 3
```

| | | | | |
|---|---|---|---|---|
| aatgctacta | ctattagtag | aattgatgcc | accttttcag | ctcgcgcccc aaatgaaaat 60 |
| atagctaaac | aggttattga | ccatttgcga | aatgtatcta | atggtcaaac taaatctact 120 |
| cgttcgcaga | attgggaatc | aactgttata | tggaatgaaa | cttccagaca ccgtacttta 180 |
| gttgcatatt | taaaacatgt | tgagctacag | cattatattc | agcaattaag ctctaagcca 240 |
| tccgcaaaaa | tgacctctta | tcaaaaggag | caattaaagg | tactctctaa tcctgacctg 300 |
| ttggagtttg | cttccggtct | ggttcgcttt | gaagctcgaa | ttaaaacgcg atatttgaag 360 |
| tctttcgggc | ttcctcttaa | tctttttgat | gcaatccgct | ttgcttctga ctataatagt 420 |
| cagggtaaag | acctgatttt | tgatttatgg | tcattctcgt | tttctgaact gtttaaagca 480 |
| tttgaggggg | attcaatgaa | tatttatgac | gattccgcag | tattggacgc tatccagtct 540 |
| aaacatttta | ctattacccc | ctctggcaaa | acttcttttg | caaaagcctc tcgctatttt 600 |
| ggttttatc | gtcgtctggt | aaacgagggt | tatgatagtg | ttgctcttac tatgcctcgt 660 |
| aattcctttt | ggcgttatgt | atctgcatta | gttgaatgtg | gtattcctaa atctcaactg 720 |
| atgaatcttt | ctacctgtaa | taatgttgtt | ccgttagttc | gttttattaa cgtagatttt 780 |
| tcttcccaac | gtcctgactg | gtataatgag | ccagttctta | aaatcgcata aggtaattca 840 |
| caatgattaa | agttgaaatt | aaaccatctc | aagcccaatt | tactactcgt tctggtgttt 900 |
| ctcgtcaggg | caagccttat | tcactgaatg | agcagctttg | ttacgttgat ttgggtaatg 960 |
| aatatccggt | tcttgtcaag | attactcttg | atgaaggtca | gccagcctat gcgcctggtc 1020 |
| tgtacaccgt | tcatctgtcc | tctttcaaag | ttggtcagtt | cggttccctt atgattgacc 1080 |
| gtctgcgcct | cgttccggct | aagtaacatg | gagcaggtcg | cggatttcga cacaatttat 1140 |
| caggcgatga | tacaaatctc | cgttgtactt | tgtttcgcgc | ttggtataat cgctgggggt 1200 |
| caaagatgag | tgttttagtg | tattcttttg | cctctttcgt | tttaggttgg tgccttcgta 1260 |
| gtggcattac | gtattttacc | cgtttaatgg | aaacttcctc | atgaaaaagt ctttagtcct 1320 |
| caaagcctct | gtagccgttg | ctaccctcgt | tccgatgctg | tctttcgctg ctgagggtga 1380 |
| cgatcccgca | aaagcggcct | ttaactccct | gcaagcctca | gcgaccgaat atatcggtta 1440 |
| tgcgtgggcg | atggttgttg | tcattgtcgg | cgcaactatc | ggtatcaagc tgtttaagaa 1500 |
| attcacctcg | aaagcaagct | gataaaccga | tacaattaaa | ggctcctttt ggagcctttt 1560 |
| ttttggagat | tttcaacgtg | aaaaaattat | tattcgcaat | ccttttagtg gtacctttct 1620 |
| attctcactc | cggccgaaact | gttgaaagtt | gtttagcaaa | atcccataca gaaaattcat 1680 |
| ttactaacgt | ctggaaagac | gacaaaactt | tagatcgtta | cgctaactat gagggctgtc 1740 |
| tgtggaatgc | tacaggcgtt | gtagtttgta | ctggtgacga | aactcagtgt tacggtacat 1800 |
| gggttcctat | tgggcttgct | atccctgaaa | atgagggtgg | tggctctgag ggtggcggtt 1860 |
| ctgagggtgg | cggttctgag | ggtggcggta | ctaaacctcc | tgagtacggt gatacaccta 1920 |

```
ttccgggcta tacttatatc aaccctctcg acggcactta tccgcctggt actgagcaaa    1980
acccgctaa tcctaatcct tctcttgagg agtctcagcc tcttaatact ttcatgtttc    2040
agaataatag gttccgaaat aggcagggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgagg    2220
attttattgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgagggag gcggttccgg tggtggctct ggttccggtg    2400
attttgatta tgaaaagatg gcaaacgcta ataaggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat cccaaatgg ctcaagtcgg tgacggtgat aattcacctt    2640
taatgaataa tttccgtcaa tatttacctt ccctccctca atcggttgaa tgtcgcctt    2700
ttgtctttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttactttct    2940
taaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttaccttt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840
ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta taacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta ttttgtttt cttgatgttt    4260
gtttcatcat cttcttttgc tcaggtaatt gaaatgaata attcgcctct gcgcgatttt    4320
```

```
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgctccta agatatttt agataaccct cctcaattcc tttcaactgt tgatttgcca    4800
actgaccaga tattgattga gggtttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta tttttaatgg cgatgttttta   4980 gggctatcag ttcgcgcatt aaagactaat agccattcaa aaatattgtc tgtgccacgt    5040
attcttacgc tttcaggtca gaagggttct atctctgttg gccagaatgt cctttttatt    5100
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640
ggggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcactgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg ccaagcttgc    6240
atgcctgcag gtcctcgaat tcactggccg tcgttttaca acgtcgtgac tgggaaaacc    6300
ctggcgttac ccaacttaat cgccttgcag cacatccccc tttcgccagc tggcgtaata    6360
gcgaagaggc ccgcaccgat cgcccttccc aacagttgcg cagcctgaat ggcgaatggc    6420
gctttgcctg gtttccggca ccagaagcgg tgccggaaag ctggctggag tgcgatcttc    6480
ctgaggccga tactgtcgtc gtcccctcaa actggcagat gcacggttac gatgcgccca    6540
tctacaccaa cgtgacctat cccattacgg tcaatccgcc gtttgttccc acggagaatc    6600
cgacgggttg ttactcgctc acatttaatg ttgatgaaag ctggctacag gaaggccaga    6660
cgcgaattat ttttgatggc gttcctattg gttaaaaaat gagctgattt aacaaaaatt    6720
```

```
taatgcgaat tttaacaaaa tattaacgtt tacaatttaa atatttgctt atacaatctt    6780 cctgttttg gggcttttct gattatcaac cggggtacat atgattgaca tgctagtttt    6840
acgattaccg ttcatcgatt ctcttgtttg ctccagactc tcaggcaatg acctgatagc    6900
ctttgtagat ctctcaaaaa tagctaccct ctccggcatt aatttatcag ctagaacggt    6960
tgaatatcat attgatggtg atttgactgt ctccggcctt tctcacccct ttgaatcttt    7020
acctacacat tactcaggca ttgcatttaa aatatatgag ggttctaaaa atttttatcc    7080
ttgcgttgaa ataaaggctt ctcccgcaaa agtattacag ggtcataatg ttttttggtac   7140 aaccgattta gctttatgct ctgaggcttt attgcttaat tttgctaatt ctttgccttg    7200
cctgtatgat ttattggatg tt                                             7222

<210> SEQ ID NO 4
<211> LENGTH: 41
<212> TYPE: DNA
<213> ORGANISM: Artificial Sequence
<220> FEATURE:
<223> OTHER INFORMATION: BamH I_SM_upper which is a primer used for
      site-directed mutation of M13KE vector

<400> SEQUENCE: 4
aaggccgctt ttgcgggatc ctcaccctca gcagcgaaag a                        41

<210> SEQ ID NO 5
<211> LENGTH: 41
<212> TYPE: DNA
<213> ORGANISM: Artificial Sequence
<220> FEATURE:
<223> OTHER INFORMATION: BamH I_SM_lower which is a primer used for
      site-directed mutation of M13KE vector

<400> SEQUENCE: 5
tctttcgctg ctgagggtga ggatcccgca aaagcggcct t                        41

<210> SEQ ID NO 6
<211> LENGTH: 90
<212> TYPE: DNA
<213> ORGANISM: Artificial Sequence
<220> FEATURE:
<223> OTHER INFORMATION: M13HK_P8_primer which is an extension primer
      used for preparation of the phage display p8 peptide library

<400> SEQUENCE: 6
ttaatggaaa cttcctcatg aaaaagtctt tagtcctcaa agcctctgta gccgttgcta    60
ccctcgttcc gatgctgtct ttcgctgctg                                     90

<210> SEQ ID NO 7
<211> LENGTH: 95
<212> TYPE: DNA
<213> ORGANISM: Artificial Sequence
<220> FEATURE:
<223> OTHER INFORMATION: M13HK_P8 which is a library oligonucleotide
      used for preparation of the phage display p8 peptide library
<220> FEATURE:
<221> NAME/KEY: variation
<222> LOCATION: (1)..(95)
<223> OTHER INFORMATION: n is a, g, c or t.
<220> FEATURE:
<221> NAME/KEY: variation
<222> LOCATION: (1)..(95)
<223> OTHER INFORMATION: m is a or c.
```

```
<400> SEQUENCE: 7
aaggccgctt ttgcgggatc cnnmnnmnnm nnmnnmnnmn nmncagcagc gaaagacagc      60
atcggaacga gggtagcaac ggctacagag gcttt                                95

<210> SEQ ID NO 8
<211> LENGTH: 97
<212> TYPE: DNA
<213> ORGANISM: Artificial Sequence
<220> FEATURE:
<223> OTHER INFORMATION: P8GB#1_upper primer used for the cloning of
      p8GB#1 phage

<400> SEQUENCE: 8
catgaaaaag tctttgtcc tcaaagcctc tgtagccgtt gctaccctcg ttccgatgct       60
gtctttcgct gctgattctt gggctgcgga tattccg                              97

<210> SEQ ID NO 9
<211> LENGTH: 97
<212> TYPE: DNA
<213> ORGANISM: Artificial Sequence
<220> FEATURE:
<223> OTHER INFORMATION: P8GB#1_lower primer used for the cloning of
      p8GB#1 phage

<400> SEQUENCE: 9
gatccggaat atccgcagcc caagaatcag gcagcgaaag acagcatcgg aacgagggta     60
gcaacggcta cagaggcttt gaggacaaag acttttt                             97

<210> SEQ ID NO 10
<211> LENGTH: 97
<212> TYPE: DNA
<213> ORGANISM: Artificial Sequence
<220> FEATURE:
<223> OTHER INFORMATION: P8GB#5_upper primer used for the cloning of
      p8GB#5 phage

<400> SEQUENCE: 10
catgaaaaag tctttgtcc tcaaagcctc tgtagccgtt gctaccctcg ttccgatgct       60
gtctttcgct gctgataatc cgattcaggc tgttccg                              97

<210> SEQ ID NO 11
<211> LENGTH: 97
<212> TYPE: DNA
<213> ORGANISM: Artificial Sequence
<220> FEATURE:
<223> OTHER INFORMATION: P8GB#5_lower primer used for the cloning of
      p8GB#5 phage

<400> SEQUENCE: 11
gatccggaac agcctgaatc ggattatcag gcagcgaaag acagcatcgg aacgagggta     60
gcaacggcta cagaggcttt gaggacaaag acttttt                             97
```